United States Patent

Kaplan

[11] 4,223,228
[45] Sep. 16, 1980

[54] DENTAL X-RAY ALIGNING SYSTEM

[75] Inventor: Jerome I. Kaplan, Indianapolis, Ind.

[73] Assignee: Indianapolis Center for Advanced Research, Indianapolis, Ind.

[21] Appl. No.: 50,705

[22] Filed: Jun. 21, 1979

[51] Int. Cl.² .............................................. H05G 1/30
[52] U.S. Cl. ................................... 250/491; 250/402; 250/416 R
[58] Field of Search ............ 250/491, 401, 402, 416 R

[56] References Cited

U.S. PATENT DOCUMENTS

| | | | |
|---|---|---|---|
| 3,839,797 | 10/1974 | Randolph | 32/67 |
| 4,012,638 | 3/1977 | Altschuler | 250/491 |
| 4,027,156 | 5/1977 | Robinet | 250/491 |

*Primary Examiner*—Craig E. Church

*Attorney, Agent, or Firm*—Woodard, Weikart, Emhardt & Naughton

[57] ABSTRACT

A dental x-ray aligning system in which various Hall effect sensors, mounted on a dental x-ray apparatus, detect the magnetic field strength resulting from a magnet which is attached to an x-ray film plate located within the mouth of a patient. By measuring and comparing the relative magnetic field strengths, the present invention can indicate when the dental x-ray apparatus is properly aligned, and can also indicate the direction in which the apparatus should be moved to obtain alignment, and the distance between the apparatus and the film plate. The present invention also includes means for adjusting the collimation of the dental x-ray apparatus.

16 Claims, 4 Drawing Figures

DENTAL X-RAY ALIGNING SYSTEM

BACKGROUND OF THE INVENTION

1. Field of the Invention

This invention relates to systems that are used for aligning a dental x-ray machine with an x-ray film plate.

2. Description of the Prior Art

Dental x-ray photography has become an invaluable diagnostic aid to the dentist and today is often routinely performed in the dental office. However, difficulties are encountered in obtaining proper alignment of the dental x-ray apparatus with an x-ray film plate because the film plate is positioned intraorally and therefore cannot be seen by the dentist or technician during the aiming process. To avoid the problem of misalignment, a larger x-ray beam size is often used. This assures that the complete film plate will be exposed; however, it also increases the hazard caused by the exposure of the patient to x-ray radiation.

Various x-ray alignment devices appear in the prior art which obtain proper positioning by mechanical means. U.S. Pat. No. 3,930,164 to Alexander discloses one such device that uses a centering rod to locate the center of the x-ray beam path and to position the subject accordingly. This particular device is used for x-rays of the temporo-mandibular joint. In U.S. Pat. No. 4,057,733 to Hofmockel discloses an x-ray image intensifier is mechanically mounted to the x-ray apparatus in such a manner that it can receive the emitted x-ray beam. The x-ray image received is reproduced on a video screen.

In German Offenlegungsschrift No. 2,134,106, to Graf there is disclosed an x-ray film plate which is positioned on a frame mounted to the x-ray apparatus.

These devices using mechanical mounting means to obtain alignment have several disadvantages in that they are uncomfortable to the patient; they are inconvenient to use and difficult to position within the mouth; they also pose a problem of sterilization. Further, the Alexander device is not adaptable for use in x-raying individual teeth within the mouth. The radioscopic device of Hofmockel involves expensive equipment. Because the Hofmockel device uses a continuous beam, the overall x-ray exposure to the patient is increased.

In the general field of x-ray alignment there are several devices which use optics in order to obtain the desired positioning. U.S. Pat. No. 4,060,733 to Franke discloses a light beam which is reflected to illuminate the area at which the x-ray machine is pointed. This is a convenient, simple aiming device however it is unsuitable to the field of dental x-rays, (because with dental x-rays neither the film position nor the teeth are typically exposed to view). U.S. Pat. No. 3,790,803 to Phillips dicloses another device that uses optics to obtain proper alignment. In Phillips a beam of light is emitted from a fixed position on the x-ray apparatus. The beam of light is reflected from a fixed position relative to the x-ray film plate. In this manner the device can indicate when there is proper alignment. U.S. Pat. No. 4,012,638 to Altschuler discloses a device which applies optics specifically to the field of dental x-ray alignment. In Altschuler a plurality of infrared emitters and detectors are positioned on the x-ray apparatus. The x-ray film plate is positioned on a frame which extends outside the mouth and has an infrared reflective surface. When the infrared light emitted is reflected back and detected then alignment is indicated. Altschuler possesses many of the disadvantages of the mechanically mounted alignment devices, in that the film plate frame necessarily has to extend outside of the mouth. This attribute presents the problems of discomfort to the patient and of difficulty in positioning the film plate in its desired location within the mouth. The Altschuler device has the further disadvantage in that it does not determine the distance between the x-ray apparatus and the x-ray film plate. This information is desirable to properly adjust the size of the x-ray beam and therefore limit the amount of x-ray exposure to the patient. This distance is typically fixed in the mechanically mounted devices.

The general area of dentistry has made use of magnets and Hall effect sensors in the past, though not in the field of x-ray alignment. U.S. Pat. No. 3,083,463 to Brooks, discloses a magnet is used in conjunction with a dental drill to produce an anesthetic effect. U.S. Pat. No. 3,839,797 to Randolph, discloses a dental drill paralleling system which uses a Hall effect sensor positioned in the field of a magnet where the magnetic field lines are substantially parallel. Proper alignment is indicated when the Hall effect sensor is parallel with the magnetic field lines.

SUMMARY OF THE INVENTION

The present invention is a simple, reliable, convenient and safe system for aiming a dental x-ray apparatus at an x-ray film plate. In the system of the present invention, magnetic field sensors, mounted on the detal x-ray apparatus, are used as a means of detecting the relative strength of a magnetic field of a magnet which is located next to an x-ray film plate within the mouth of a patient. By measuring and comparing the relative strengths of this magnetic field the system of the present invention can detect and indicate the condition of alignment or misalignment. Certain embodiments of the present invention also indicate the direction in which the apparatus should be moved in order to obtain a desired alignment and indicate the distance between the apparatus and the x-ray film plate.

It is an object of the present invention to provide a simple and reliable system for aligning a dental x-ray apparatus with an x-ray film plate.

It is a further object of the present invention to provide a dental x-ray apparatus aligning system that is both convenient to use and comfortable for the patient.

It is a further object of the present invention to provide a dental x-ray aligning system that is an aid in reducing the overall x-ray exposure to the patient.

It is a further object of certain embodiments of the invention to provide a dental x-ray aligning system that not only indicates the condition of alignment but also indicates the direction in which the apparatus should be moved in order to obtain alignment and indicates the distance between the dental x-ray apparatus and an x-ray film plate.

These and other objects and advantages of the present invention will become more apparent from the following detailed description and accompanying drawings.

DESCRIPTION OF THE PREFERRED EMBODIMENT

Figure 1:
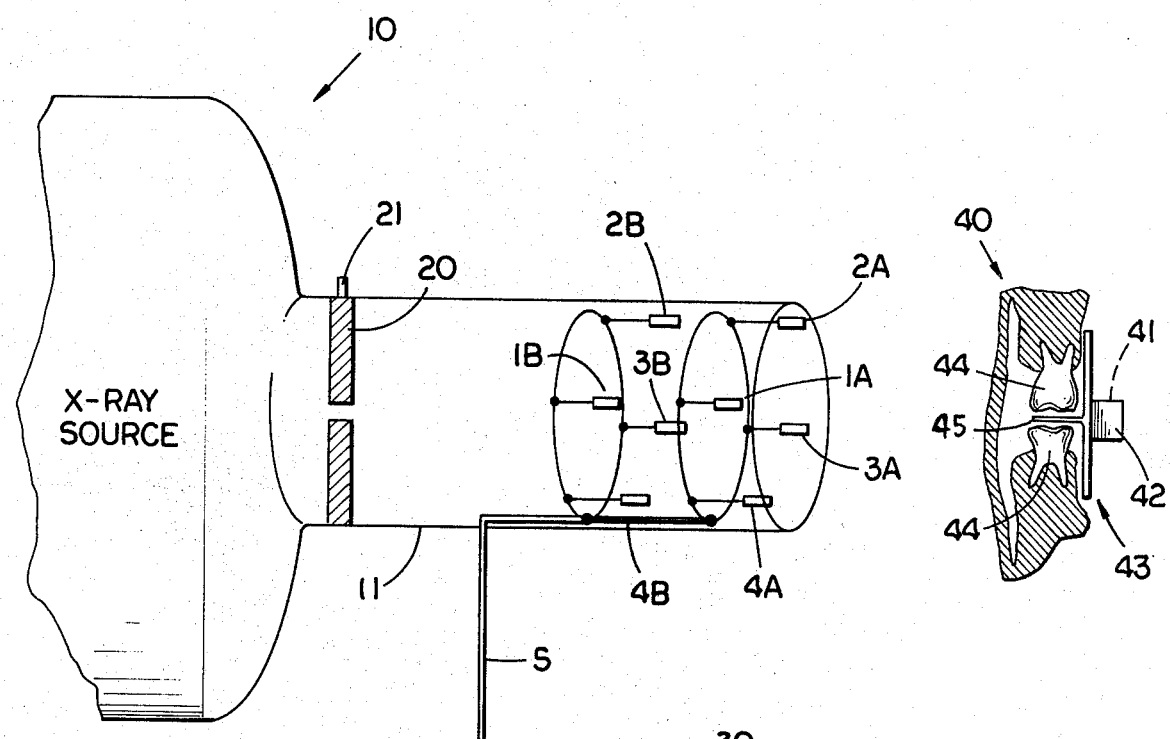
FIG. 1 is a schematical view showing an embodiment of the present invention in position for use in aiming a dental x-ray apparatus at an x-ray film plate located within the mouth of the patient.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
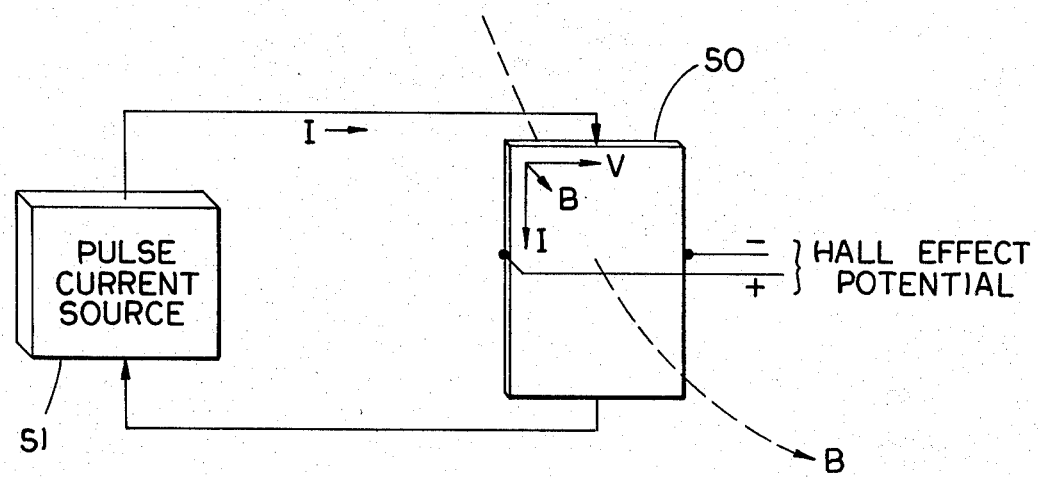
FIG. 3 illustrates a Hall effect probe connected with a pulse current source, and located within a magnetic field.

FIG. 3 illustrates a current (I) passing through a Hall effect sensor 50, which is simply a rectangular strip of conductive or semiconductive material. The "Hall effect" is used as a simple and reliable means for measuring the strength of a magnetic field. The principle of the Hall effect is that if an electrical current (I) passes through a magnetic field (B), then there will be a voltage differential generated across the width of the conductor. This voltage differential is known as the Hall effect potential. The magnitude of the Hall effect potential is reflective of the strength of the current passing through the sensor and the magnetic field which is perpendicular to the sensor. Therefore, if the current is known, then the Hall effect potential measures the strength of the magnetic field. In this way Hall effect sensors are used to detect and measure the strength of a magnetic field.

In the preferred embodiment, a pulse current source 51 pulsates a specific direct current Hall effect probes 1A-B, 2A-B, 3A-B and 4A-B (illustrated in FIG. 3 as Hall effect probe 50). It has been found that use of pulse currents allows a greater peak current to pass through the probes without overheating thus giving the system greater sensitivity and stability.

In the preferred embodiment of the present invention a magnet 41 of samarium cobalt is placed in a receptacle 42 that is located on the back central portion of x-ray film plate 43. It is preferable that the magnet be strong in order to avoid the necessity of using exceptionally sensitive Hall effect probes which are relatively expensive. Although a small receptacle 42 is used to maintain the magnet in place in the preferred embodiment, any means which satisfactorily maintains the magnet 41 in fixed relation to the x-ray film plate 43 is acceptable. In the preferred embodiment, the north-south axis of magnet 41 is perpendicular to x-ray film plate 43. It is preferred that the alignment process take place in a portion of the magnetic field of the magnet where the magnetic force lines are not substantially parallel. The problems occuring as a result of aligning the apparatus in a substantially parallel portion of the magnetic field of the magnet will be discussed later in this detailed description.

During the x-ray procedure, x-ray film plate 43 is positioned within the mouth 40 of a patient. The position of x-ray film plate 43 is maintained by the patient's clenching of his teeth 44 against tab 45 which projects perpendicularly from the plane of the film plate. It is preferred that the size of x-ray film plate 43 be such so that it fits comfortably within the mouth 40 of a patient. Therefore, it is preferred that the x-ray film plate not exceed 5 centimeters in any direction.

In the preferred embodiment two sets of four probes each are mounted on the x-ray apparatus. The first set of probes 1A, 2A, 3A and 4A are equally angularly spaced about the circumference of the cylindrical x-ray cone 11 of the dental x-ray apparatus 10. Probes 1A and 3A located on opposite sides of x-ray cone 11 are also positioned parallel to each other. Likewise probes 2A and 4A are positioned parallel to each other.

The second set of probes are also equally angularly spaced about the circumference of the cylindrical x-ray cone 11 and are located approximately five centimeters back from the first set of probes. Some advantages in construction and sensitivity are achieved by spacings of from 2 to 10 centimeters. Probes 1B and 3B and probes 2B and 4B are parallel to each other, respectively. Further, probes 1B and 3B are positioned on the same horizontal plane as probes 1A and 3A, and probes 2B and 4B are positioned on the same vertical plane as probes 2A and 4A. Thus the combination of the four probes 1A, 1B, 3A and 3B form the basis for detecting horizontal alignment and the combination of the four probes 2A, 2B, 4A and 4B form the basis for detecting vertical alignment. For ease of illustration, probes 1A-B and 2A-B, 3A-B and 4A-B are shown rotated slightly, appearing not to be on a single horizontal and vertical plane in which they actually are positioned.

Pulsating direct current is passed through the probes 1A-D and 2A-D through lines 5. Lines 5 also transmit the Hall effect potentials to indicator circuitry 30.

Indicator circuitry 30 receives the Hall effect potentials and compares their relative values. This is accomplished by using simple comparator circuitry which is commonly known by those having a basic understanding of electronics.

Figure 4:
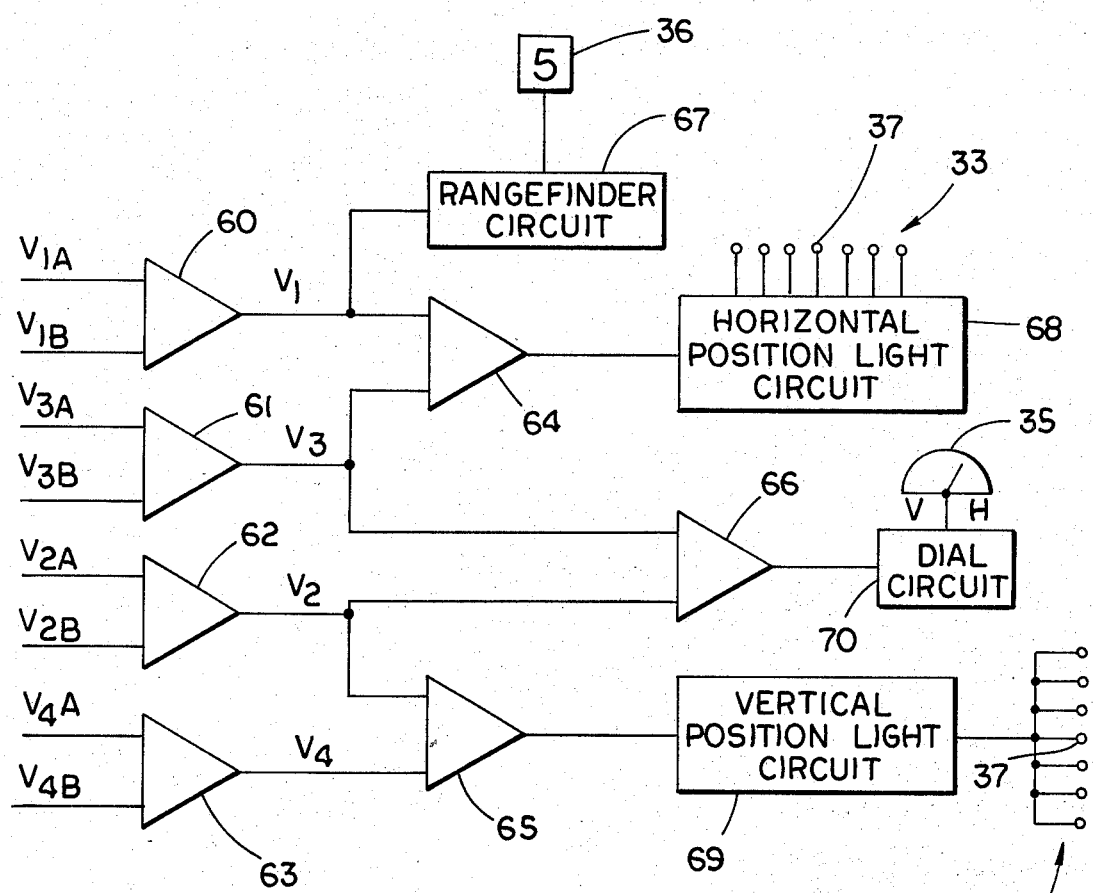
FIG. 4 is a schematical diagram of the internal circuit of the indicator circuitry of FIG. 1.

The Hall effect probes are sensitive not only the magnetic field of magnet 41, but also to the Earth's magnetic field. For this reason, the second set of probes are positioned sufficiently far away from magnet 41 so that they are primarily sensitive only to the earth's magnetic field. Therefore, in order to obtain the actual magnetic field strength resulting from magnet 41, the Hall effect potentials of each probe in the first set is compared with the Hall effect potentials of the corresponding probes in the second set. For example and as illustrated in FIG. 4, the Hall effect potential at probe 1A ($V_{1A}$) is compared with the Hall effect potential at probe 1B ($V_{1B}$) to obtain the magnetic field strength perpendicular to probe 1A solely resulting from magnet 41 ($V_1 = V_{1A} - V_{1B}$). Likewise, $V_{3A}$ and $V_{3B}$ are compared to obtain a voltage output $V_3$. The resulting two horizontal outputs ($V_1$ ($V_{1A} - V_{1B}$) and $V_3$ ($V_{3A} - V_{3B}$) are then compared and the condition of horizontal alignment is indicated when the compared outputs are equal. Likewise when the voltage outputs $V_2$ ($V_{2A} - V_{2A}$) and $V_4$ ($V_{4A} - V_{4B}$) are equal to each other then vertical alignment is indicated.

Figure 2:
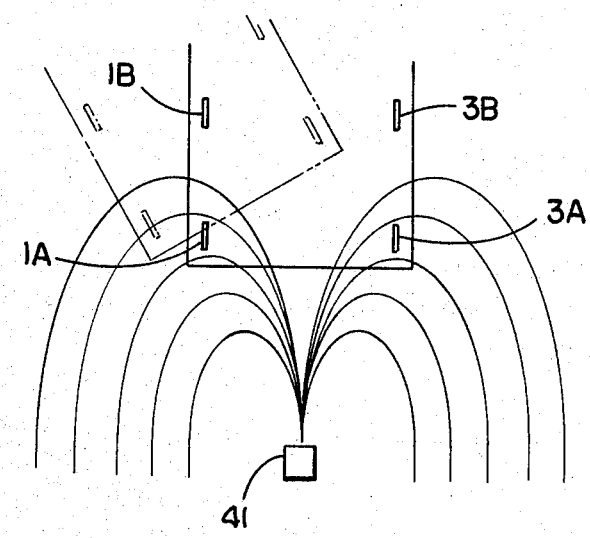
FIG. 2 is a horizontal cross-sectional view showing the magnetic field lines of a magnet and two relative positions of a dental x-ray apparatus mounted with Hall effect probes.

FIG. 2 illustrates a cross sectional view of the dental x-ray apparatus 10 in horizontal alignment with magnet 41, and shows some of the magnetic field lines emanating from magnet 41. Also shown, in broken lines, is dental x-ray apparatus 10 in horizontal misalignment.

Because the Hall effect probes only detect the magnetic field which is perpendicular to the probes there are possible positions of the dental x-ray apparatus 10 in which the mere comparison of $V_1$ with $V_3$ and $V_2$ with $V_4$ creates a false indication of alignment. This occurs where one of the probes (3A, for instance) although further from magnet 41 is nearly perpendicular to the magnetic field and the corresponding probe (1A) is nearly parallel to the magnetic field and therefore indicates a comparatively small magnetic field even though the probe is close to the magnet. In the preferred embodiment the problem is resolved by comparing $V_3$ with $V_2$. If $V_3$ is greater than $V_2$ then the horizontal plane is not in alignment. If $V_2$ is greater than $V_3$ then the vertical plane is not properly aligned.

This misalignment problem would be more significant if the north-south axis of magnet 41 were parallel to the film plate rather than perpendicular to it, because there would be numerous misalignment positions which are only slightly out of alignment and therefore more difficult to detect.

Indicator circuitry 30 has a display 32 which indicates the condition of alignment; the direction in which apparatus 10 should be moved in order to obtain alignment; and the distance between apparatus 10 and film plate 43. Horizontal position lights 33 and vertical position lights 34 form a 7 by 7 cross. The results of the comparison of $V_1$ and $V_3$ cause one of the horizontal LED position lights 33 to turn on. If $V_1$ equals $V_3$, then the central position light 37 is on, indicating horizontal alignment. If another horizontal position light is on instead, then apparatus 10 is not properly aligned, and must be moved generally in the opposite direction from which the lit position light is located on the display in order to obtain alignment. Thus, if a horizontal position light is on that is to the right of center on display 32, then apparatus 10 must generally be moved to the left to obtain alignment. The further the lit position light is from the center of display 32, the further apparatus 10 is out of alignment.

The vertical position lights 34, function in the same manner with respect to vertical alignment as the horizontal position lights 33 operate to indicate horizontal alignment. Thus, proper alignment is initially indicated when only the central position light 37 is lit.

However, as previously mentioned, a false indication of alignment may be given even though $V_1 = V_3$ and $V_2 = V_4$. Therefore $V_3$ is compared with $V_2$, and the results of this comparison are indicated on dial 35. If $V_3 = V_2$, then dial 35 points directly upward, indicating that apparatus 10 is in proper alignment. If $V_3$ is greater than $V_2$, then dial 35 points toward the H on display 32, indicating horizontal misalignment. Likewise, if $V_2$ is greater than $V_3$, then dial 35 points toward the V on display 32, indicating vertical misalignment.

Rangefinder display 36 indicates the distance between apparatus 10 and film plate 43. This is simply done by measuring the level of $V_1$ and displaying the result digitally.

Once the range is known, and the size of the x-ray film plate 43 is known, the x-ray beam size may be adjusted to the precise minimum size possible to allow for satisfactory results. As shown in FIG. 1, the x-ray apparatus includes a variable aperture 20 with a manually operable control lever 21. Aperture 20 and lever 21 serve as a variable collimation means for adjusting the x-ray beam size of the dental x-ray apparatus 10.

FIG. 4 is a schematical diagram of the simple comparator circuitry that is contained in indicator circuitry 30, indicating the voltage comparisons that are made and the manner in which they interrelate with display 32.

FIG. 4 shows comparator circuits 60 through 66 each having two inputs and an output. Comparator circuit 60 receives at its inputs Hall effect potentials $V_{1A}$ and $V_{1B}$ and produces and output voltage $V_1$. Likewise comparator circuit 61 receives at its inputs Hall effect potentials $V_{3A}$ and $V_{3B}$ and produces a voltage output $V_3$; comparator circuit 62 receives at its inputs Hall effect potentials $V_{2A}$ and $V_{2B}$ and produces a voltage output $V_2$; comparator circuit 62 receives at its inputs Hall effect potentials $V_{4A}$ and $V_{4B}$ and produces a voltage output $V_4$. Voltage outputs $V_1$ and $V_3$ are inputted to comparator circuit 64. The output of comparator circuit 64 is connected to horizontal position lights circuit 68. Voltage outputs $V_2$ and $V_4$ are inputted into comparator circuit 65. The output of comparator circuit 65 is connected to vertical position lights circuit 69. Voltage outputs $V_2$ and $V_3$ are inputted to comparator circuit 66. Dial circuit 70 connects with the dial 35 of display 32. The output of comparator circuit 66 connects with dial circuit 70.

The output of comparator circuit 60 is connected with rangefinder circuit 67. Rangefinder circuit 67 is connected with the rangefinder display 36 of display 32. Horizontal position lights circuit 68 is connected with the horizontal position lights 33 of display 32, including central position light 37. Vertical position light circuit 69 is connected with the vertical position lights 34 of display 32, including central position light 37. It can be noted that light 37 of display 33 is the same light which is identified as light 37 of display 34, although illustrated separately in FIG. 4 for purposes of clarity.

While there are illustrated a set of eight Hall effect detectors, a less precise alignment device could be built with as few as 3 detectors.

While there have been described above the principles of this invention in connection with a specific apparatus, it is to be clearly understood that this description is made only by was of example and not as a limitation as to the scope of the invention.

What is claimed is:

1. A dental x-ray aligning system for aiming a dental x-ray apparatus at an x-ray film plate comprising:
   a. a magnet;
   b. magnet positioning means for maintaining said magnet in a fixed relation with an x-ray film plate;
   c. at least three Hall effect probes;
   d. probe positioning means for maintaining said Hall effect probes in fixed relation to the dental x-ray apparatus;
   e. current means for passing a specific current through said Hall effect probes;
   f. detection means for detecting and measuring the Hall effect voltage potentials of said probes; and
   g. indicator means for comparing the detected Hall effect voltage potentials of said probes and for indicating alignment of the dental x-ray apparatus with the x-ray film plate.

2. The dental x-ray aligning system of claim 1 in which said indicator means additionally includes direction means for indicating the direction in which the x-ray apparatus should be moved in order to align the dental x-ray apparatus with the x-ray film plate.

3. The dental x-ray aligning system of claim 1 in which said indicator means additionally includes rangefinder means for indicating the distance from the dental x-ray apparatus to the x-ray film plate.

4. The dental x-ray aligning system of claim 3 additionally comprising:
   h. collimation means for adjusting the x-ray beam size of the dental x-ray apparatus.

5. The dental x-ray aligning system of claim 1 in which said magnet is a permanent magnet of samarium cobalt.

6. The dental x-ray aligning system of claim 1 in which said magnet positioning means comprises a container attached to the central back portion of the x-ray film plate.

7. The dental x-ray aligning system of claim 1 in which the magnet positioning means maintains said magnet in a position such that the north-south polar axis of said magnet is perpendicular to the x-ray film plate.

8. The dental x-ray aligning system of claim 1 additionally comprising:
   i. means for maintaining the x-ray film plate in fixed relation to a tooth within the mouth of a patient, said means including a tab which projects perpendicularly from the x-ray film plate.

9. The dental x-ray aligning system of claim 1 in which said plurality of Hall effect probes includes a first set of probes and a second set of probes and in which said probe positioning means maintains said Hall effect probes such that:
   a. said first set of probes are approximately equally angularly spaced along the circumference of a first circle, which is perpendicular to an x-ray beam emitted from the dental x-ray apparatus.
   b. said second set of probes are approximately equally angularly spaced along the circumference of a second circle which is spaced a distance away from said first circle.
   c. said first circle and said second circle have about the same radius.

10. The dental x-ray aligning system of claim 1 in which said Hall effect probes include strips of electrically conductive material and said probe positioning means maintains said probes such that the plane defined by the surface of each said probe is substantially parallel to an x-ray beam emitted from the dental x-ray apparatus.

11. The dental x-ray aligning system of claim 9 in which said Hall effect probes include strips of electrically conductive material and said probe positioning means maintains said probes such that the plane defined by the surface of each said probe is substantially parallel to an x-ray beam emitted from the dental x-ray apparatus.

12. The dental x-ray aligning system of claim 9 in which said first set of probes includes 4 probes and said second set of probes includes 4 probes.

13. The dental x-ray aligning system of claim 9 in which the distance between said first circle and said second circle is from 2 to 10 centimeters.

14. The dental x-ray aligning system of claim 1 in which said current means passes a direct current through said Hall effect probes.

15. The dental x-ray aligning system of claim 14 in which the direct current of said current means pulsates.

16. A dental x-ray aligning system for aiming a dental x-ray apparatus at an x-ray film plate comprising:
   a. a magnet;
   b. magnet positioning means for maintaining said magnet in a fixed relation with an x-ray film plate;
   c. at least three magnetic field sensors;
   d. probe positioning means for maintaining said magnetic field sensors in fixed relation to the dental x-ray apparatus;
   e. detection means for detecting and measuring magnetic field strengths sensed by said magnetic field sensors; and
   f. indicator means for comparing the detected magnetic field strengths and for indicating alignment of the dental x-ray apparatus with the x-ray film plate.

* * * * *